United States Patent [19]

Monkovic et al.

[11] 4,052,389
[45] Oct. 4, 1977

[54] DERIVATIVES OF 9,10-DIHYDROXY-1-(p-ALKOXYBENZYL)-PERHYDROISOQUINOLINE OXAZINE-3-ONE

[75] Inventors: Ivo Monkovic, Candiac; Carol Bachand, Cote Ste-Catherine; Henry Wong, Candiac, all of Canada

[73] Assignee: Bristol-Myers Company, New York, N.Y.

[21] Appl. No.: 669,540

[22] Filed: Mar. 23, 1976

[51] Int. Cl.$^2$ ............... C07D 265/00; C07D 273/00; C07D 295/00
[52] U.S. Cl. .................................................. 544/89
[58] Field of Search ................................. 260/244 R

[56] References Cited

U.S. PATENT DOCUMENTS

| | | | |
|---|---|---|---|
| 3,466,288 | 9/1969 | Hansen et al. | 260/244 R |
| 3,775,414 | 11/1973 | Monkovic et al. | 260/285 |
| 3,819,635 | 7/1974 | Pachter et al. | 260/285 |
| 3,905,956 | 9/1975 | Derieg et al. | 260/244 |
| 3,919,237 | 11/1975 | Halder | 260/285 |

OTHER PUBLICATIONS

Chem. Abst. 77, 56400(n) (1972) Elliott et al.

*Primary Examiner*—Albert T. Meyers
*Assistant Examiner*—D. W. Robinson
*Attorney, Agent, or Firm*—Robert H. Uloth

[57] ABSTRACT

The disclosed invention is to a compound of the formula:

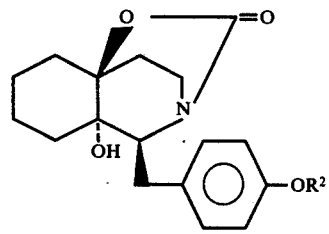

in which $R^2$ is lower alkyl. These compounds are useful in the preparation of N-substituted-14-hydroxy-3-substituted morphinan derivatives which have been found to possess potent narcotic agonist or antagonist activity.

2 Claims, No Drawings

4,052,389

DERIVATIVES OF 9,10-DIHYDROXY-1-(P-ALKOXYBENZYL)-PERHYDROISOQUINOLINE OXAZINE-3-ONE

DESCRIPTION OF THE PRIOR ART

1. U.S. Pat. No. 3,775,414 describes a process for the preparation of the identical compounds prepared by the process claimed herein.

2. U.S. Pat. No. 3,819,635 describes another process for the preparation of the identical compounds prepared by the process claimed herein.

3. Onda et al., Chem. Pharm. Bull. 21, 2359–2365 (1973) report the epoxidation of 1-(p-methoxybenzyl)-2-methyl-1,2,3,4,5,6,7,8-octahydroisoquinoline to produce the two epimeric epoxides

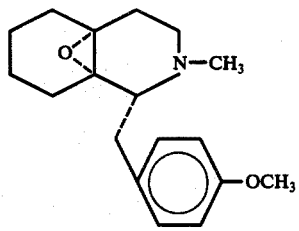

and

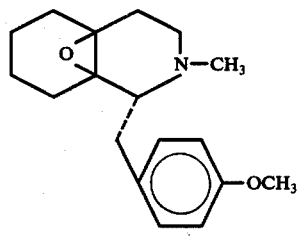

and the diols resulting therefrom having the formulas

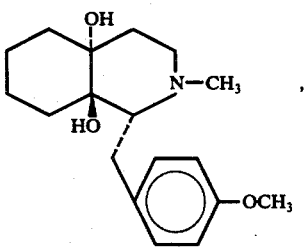

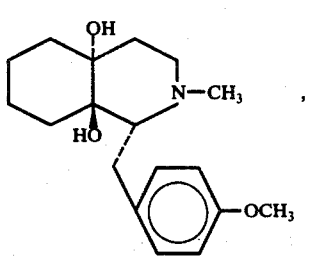

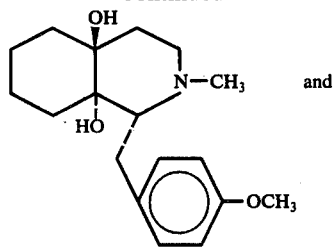

and

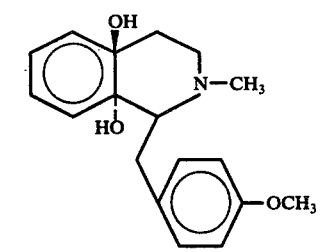

Nothing in this paper describes, anticipates or teaches the preparation of the 9,10-diols in which the N-methyl is H, or an alkanoyl as described herein. Furthermore, it is significant that the authors' goal was to synthesize 14-hydroxymorphinans via these diol intermediates and that they failed in their attempts, whereas the instant inventors have succeeded.

4. Schnider and Hellerback, Helv. Chim. Acta., 34, 2218–2222 (1951) describe the preparation of morphinans from the same starting materials as used in the instant invention. Nothing is taught or suggested that 14β-hydroxymorphinans could be prepared via this route.

5. Schnider, Brossi and Vogler, Helv. Chim. Acta., 37, 710–720 (1954) further describe the preparation of 14-deoxymorphinans from the same starting materials as used in the instant invention. Again, nothing is taught or suggested that 14β-hydroxymorphinans could be prepared via this route.

6. Schnider and Hellerback, Helv. Chim. Acta. 33, 1437–1448 (1950) describe the preparation of 14-deoxymorphinans from the same starting materials as used in the instant invention. Again, nothing is taught or suggested that 14β-hydroxymorphinans could be prepared via this route.

7. U.S. Pat. No. 3,919,237 reports the cyclization of compounds having the formulas

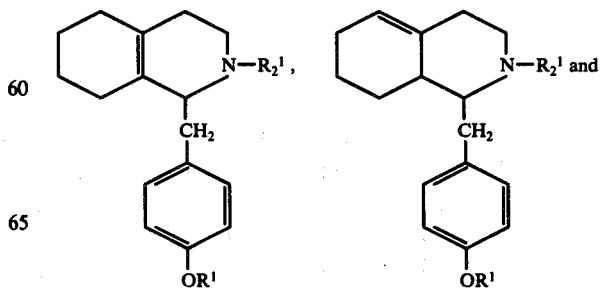

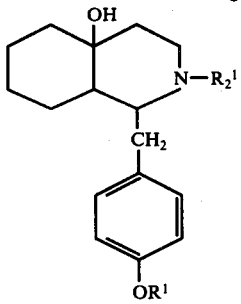

and derivatives thereof into isomorphinans and morphinans using boron trifluoride and a proton/hydronium ion donor as the cyclization catalyst. None of the compounds so produced have a 14β-hydroxy substituent.

SUMMARY OF THE INVENTION

A new process for the preparation of compounds having the formula

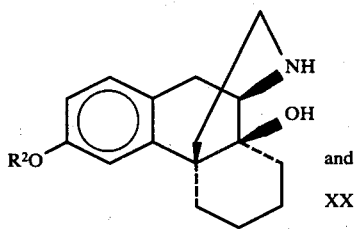

and XX

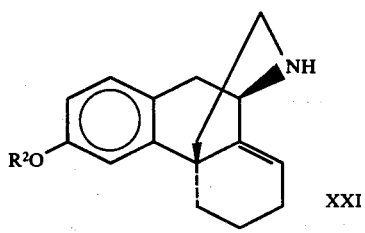

XXI wherein $R^2$ is H or (lower)alkyl; or an acid addition salt thereof from the starting material 2-(p-methoxybenzyl)-1,2,3,4,5,6,7,8-octahydroisoquinoline is disclosed.

This invention relates to a new and novel synthesis of 14-hydroxy-3-substituted morphinan derivatives having the formula

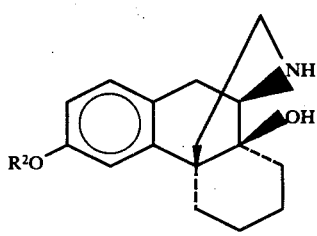

XX

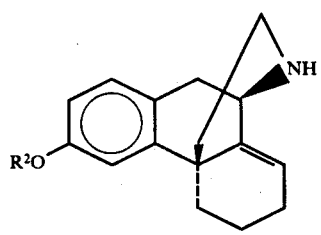

XXI in which $R^2$ is H or (lower)alkyl; which compounds are further transformable into the compounds having the formula

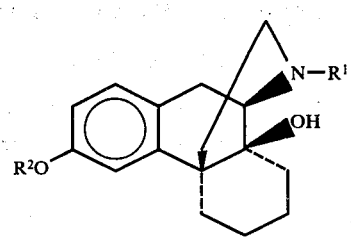

L in which $R^1$ is cyclopropylmethyl and cyclobutylmethyl and $R^2$ is H or (lower)alkyl; or a pharmaceutically acceptable salt thereof.

Drug abuse by thrill-seeking youth or by people looking for an escape from the realities of everyday life has become more and more common place in our present society. One class of widely abused drugs are the narcotic analgetics such as codeine, morphine, meperidine, etc. It is because of the high addictive potential of these agents that much time and money are being expended by the pharmaceutical industry and by governments to try and discover and develop new nonaddicting analgetics and/or narcotic antagonists.

It was an object of the present invention to develop a method of synthesis for the above-described Compounds XXI and XX that would not be dependent upon opium alkaloids as starting materials and yet would be commercially feasible.

The objectives of the present invention have been achieved by the process of preparing the compounds of Formula I by their total synthesis from the readily available starting material.

The compounds of the instant invention have the basic morphinan nucleus which is numbered and represented by the following plane formula:

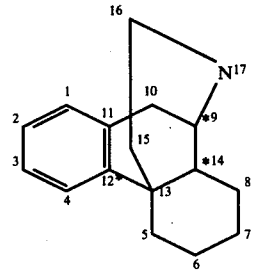

Although there are three asymmetric carbons (asterisks) in the morphinan molecule, only two diastereoisomeric (racemic) forms are possible, because the iminoethano system, attached to position 9 and 13, is geometrically contained to a cis-(1,3-diaxial)-fusion. These racemates can, therefore, differ only at the junction of rings B and C — in other words, in the configuration of carbon 14. The only variable will be the cis and trans relationship between the 5 (13) and 8 (14) bonds (Analgetics, Ed. George de Stevens, Academic Press, New York, p. 137 (1965)).

When in the compounds of the present invention, the (13) and 8 (14) bonds are cis to each other, we have compounds commonly designated as "morphinans". The use of a graphic representation of a "morphinan" is meant to include the dl racemic mixture and the resolved d and l isomers thereof.

The "morphinan" compounds of the present invention can each exist as two optical isomers, the levorotatory and dextrorotatory isomers. The optical isomers can be graphically illustrated as:

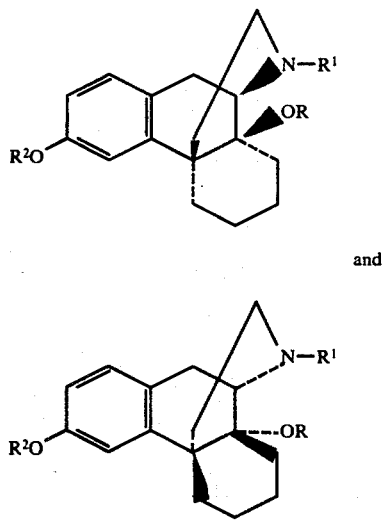

and

The present invention embodies all of the morphinan isomers including the optical isomers in their resolved form.

The optical isomers can be separated and isolated by fractional crystallization of the diastereoisomeric salts formed, for instance, with d- or l-tartaric acid or D-(+)-α-bromocamphor sulfonic acid. The levorotatory isomers of the compounds of the present invention are the most preferred embodiments.

For the purpose of this disclosure, the term "(lower)alkyl" is defined as an alkyl radical containing 1 to 6 carbon atoms. "(lower)alkenyl" is defined as a hydrocarbon radical of 3 to 7 carbons containing one double bond. The term "(lower)acyl" is an acyl radical of 2 to 6 carbon atoms, e.g., acetyl, propionyl, isobutyryl, etc. The term "pharmaceutically acceptable acid addition salt" is defined to include all those inorganic and organic acid salts of the compounds of the instant invention, which salts are commonly used to produce nontoxic salts of medicinal agents containing amine functions. Illustrative examples would be those salts formed by mixing the compounds of Formula I with hydrochloric, sulfuric, nitric, phosphoric, phosphorous, hydrobromic, maleic, malic, ascorbic, citric or tartaric, pamoic, lauric, stearic, palmitic, oleic, myristic, lauryl sulfuric, naphthalenesulfonic, linoleic or linolenic acid, and the like.

The compounds XX and XXI of the instant invention are prepared by a total synthesis comprising 5 steps. The synthesis is efficient and appears commercially feasible. The process is outlined in Chart I

CHART I

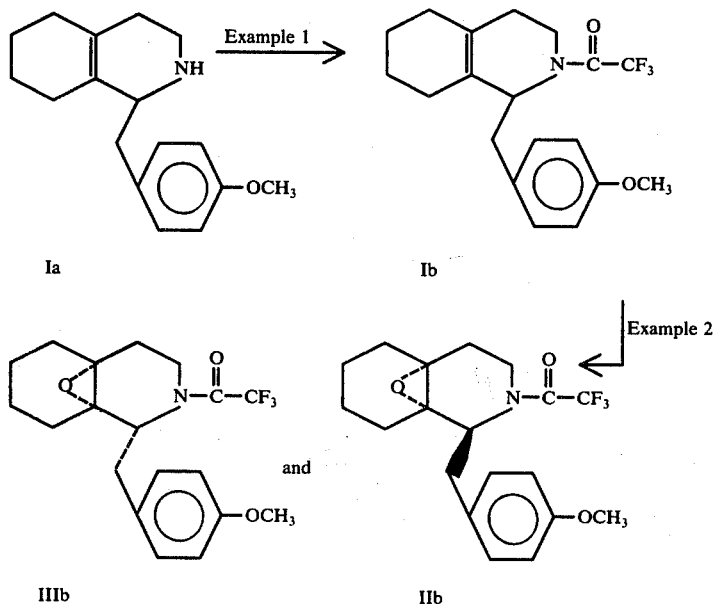

CHART I -continued
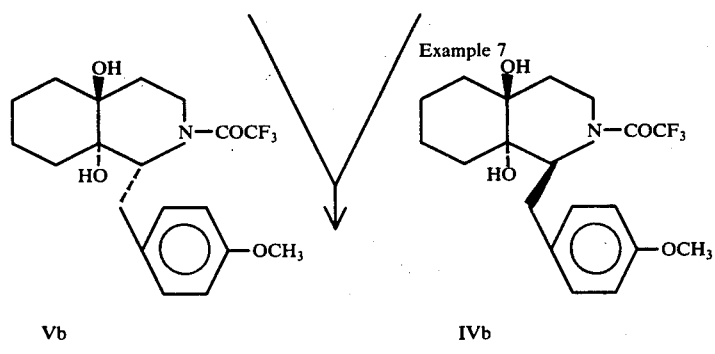
Vb      Example 7      IVb
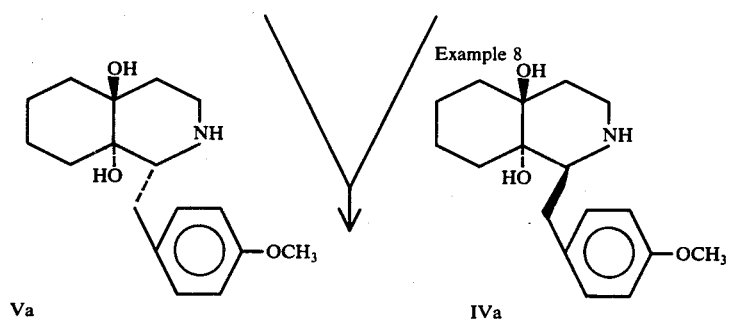
Va      Example 8      IVa
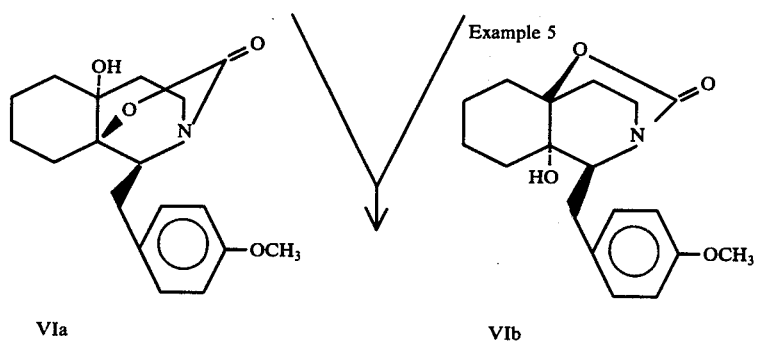
VIa      Example 5      VIb
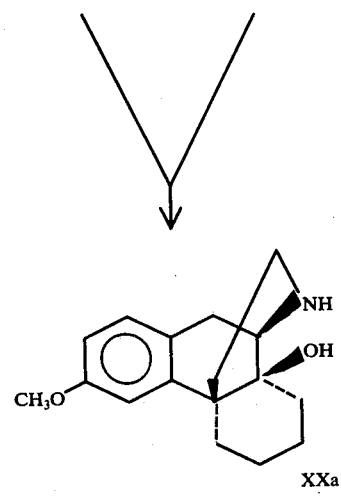
XXa CHART I -continued

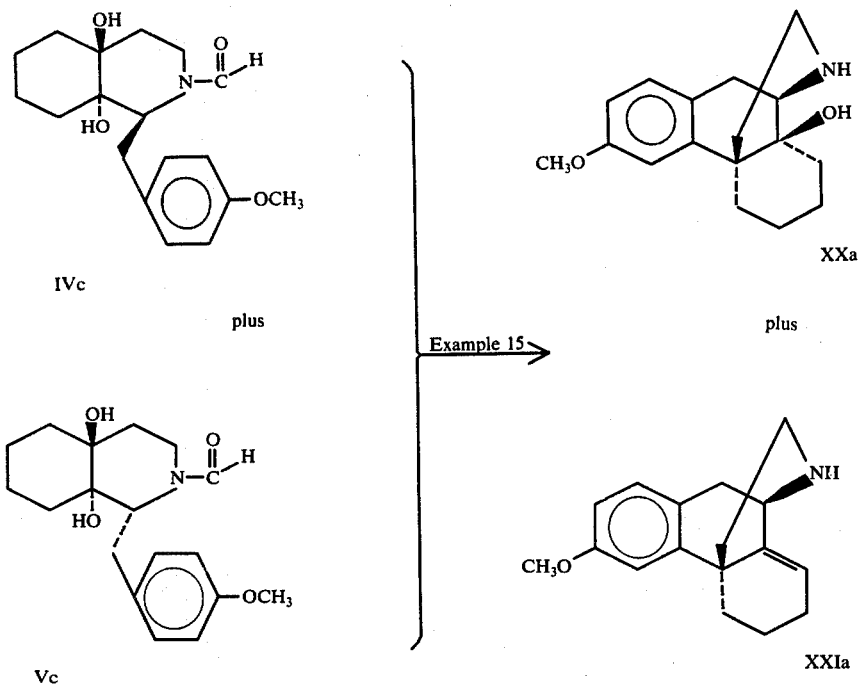

IVc plus

Vc

Example 15 → plus

XXa

XXIa

For the purpose of this disclosure the term "inert organic solvent" means an organic solvent that does not participate in the reaction to the extent that it emerges unchanged from the reaction. Such solvents are methylene chloride, chloroform, dichloroethane, tetrachloromethane, benzene, toluene, ether, ethyl acetate, xylene, tetrahydrofuran dioxane, dimethylacetamide, and the like when an acid halide is employed. When an alkylation reaction is being performed, the inert solvent used may also include (lower)alkanols such as methanol, ethanol, n-propanol, isopropanol and the like.

Compound XXI is readily converted to compound XX or compound L by the processes and examples found in U.S. Pat. No. 3,819,635, which issued June 25, 1974.

The term "organic tertiary amine" means a tertiary amine commonly employed as a proton acceptor in alkylation and acylation reactions. Such amines are tri(lower)alkylamines, e.g., trimethylamine, triethylamine and the like, pyridine, dimethylaniline, N-methylpiperidine, and the like.

A preferred embodiment of the present invention is the process for the preparation of compounds having the formulas

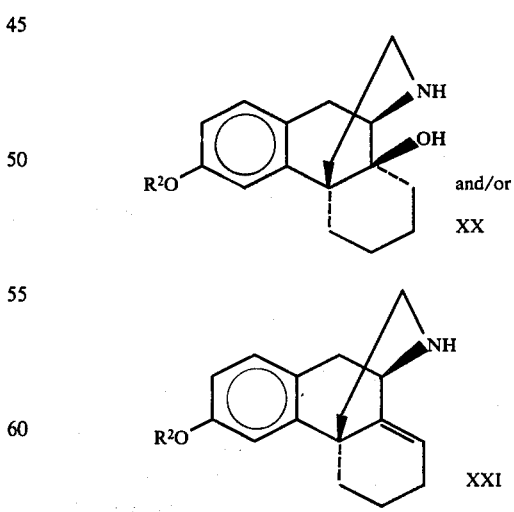

and/or XX

XXI wherein $R^2$ is (lower)alkyl; which process consists of the step of treating the compound having the formulas

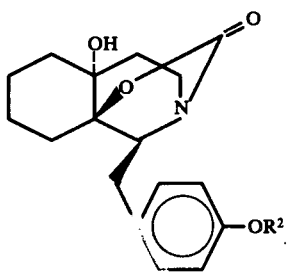 VIa,

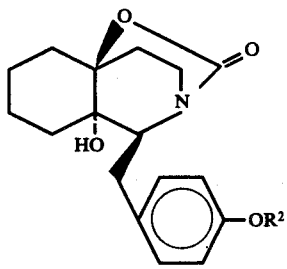 VIb,

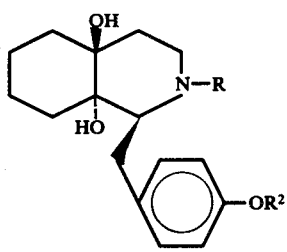 IV or

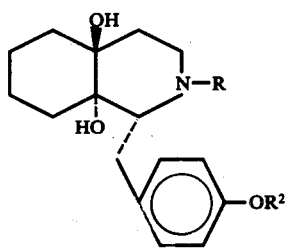 V in which R² is (lower)alkyl and R is H or a radical of the formula

wherein X is H, CF₃, —OR³ or R³ in which R³ is (lower-)alkyl or a radical having the formula

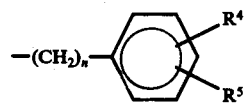

wherein n is an integer of 0 to 5, R⁴ and R⁵ are alike or different and each is H, Cl, Br, F, CF₃, NO₂, OH, (lower)alkyl or (lower)alkoxy with a strong acid to produce the compounds having the formulas XX and XXI.

A more preferred embodiment is the process of preparing compound XX, which process consists of the consecutive steps of A. treating the compounds having the formulas

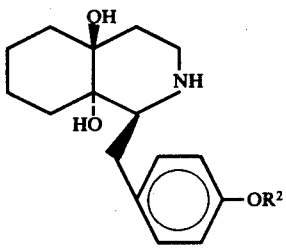 IVa and

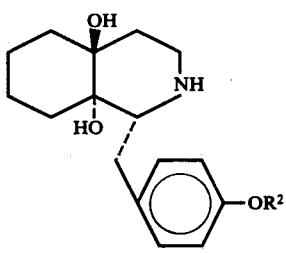 Va in which R² is (lower)alkyl with phosgene in the presence of a tertiary amine to produce the compounds having the formulas

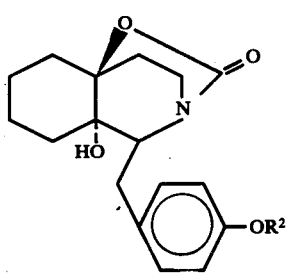 VIb and

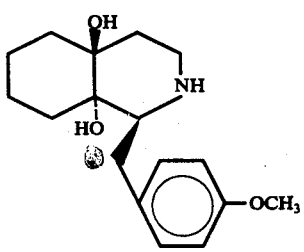 VIa in which R² is as defined above; and

B. heating compounds VIa and VIb with a strong acid to produce the compound XX.

A most preferred embodiment is the process for the preparation of the compound having formula XX in which R² is methyl, which process comprises the steps of A. treating the compound having the formula

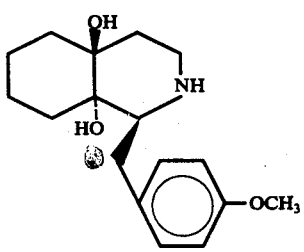 IVa' with a slight molar excess of phosgene in the presence of at least a two molar excess of a tertiary amine selected from the group consisting of triethylamine, pyridine, trimethylamine, dimethylaniline and N-methylpiperidine in tetrahydrofuran at a temperature in the range of about −15° C. to +35° C. to produce the compounds having the formulas

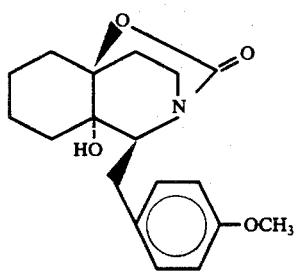

VI′b

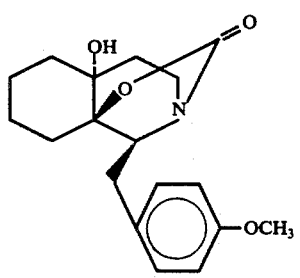

VI′a

;and

B. heating compounds VI′ in polyphosphoric acid for at least 72 hours to produce compound XX in which $R^2$ is methyl.

Another preferred embodiment is the process for the preparation of the compounds having the formulas XX and XXI, which process comprises the step of treating the compounds having the formulas

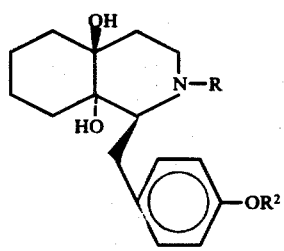

IV or

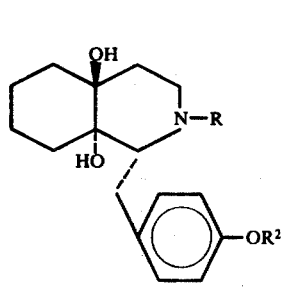

V in which $R^2$ is (lower)alkyl and R is trifluoroacetyl, carbo(lower)alkoxy or formyl, with a strong acid to produce the compounds having the formulas XX or XXI.

A most preferred embodiment is the process for the preparation of compounds XX and XXI in which $R^2$ is methyl, which process comprises the step of treating the compounds having the formulas

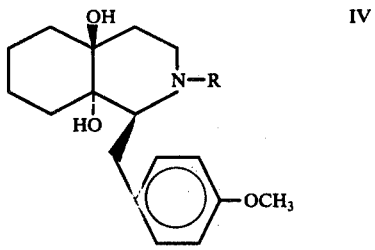

IV

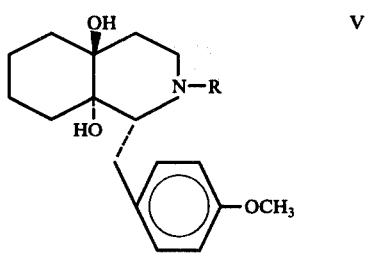

V in which R is formyl, carbomethoxy or trifluoroacetyl with polyphosphoric acid or phosphoric acid with the aid of heat to produce the compounds XX and XXI in which $R^2$ is methyl.

A preferred embodiment of the present invention is the compound having the formula

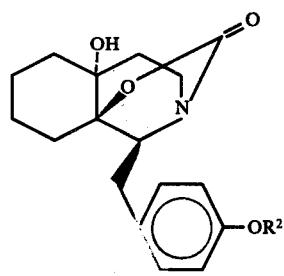

or

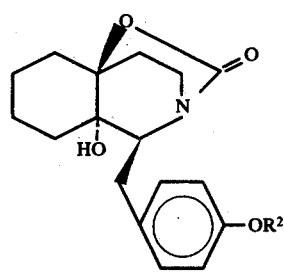

in which $R^2$ is (lower)alkyl.

A most preferred embodiment is the compound having the formula

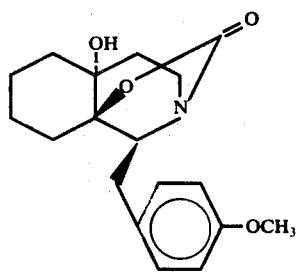

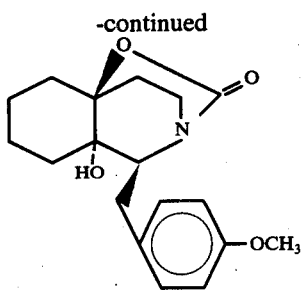

A preferred embodiment of the present invention is the compound having the formula

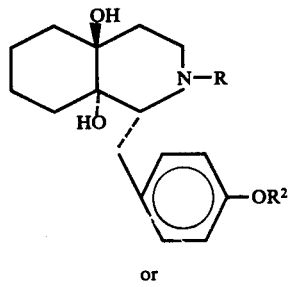

or

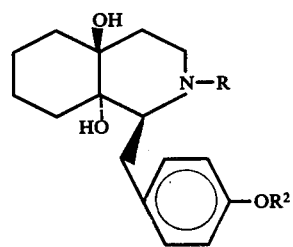

wherein $R^2$ is (lower)alkyl, R is H or a radical of the formula

wherein X is H, $CF_3$, $-OR^3$ or $R^3$ in which $R^3$ is (lower)alkyl or a radical having the formula

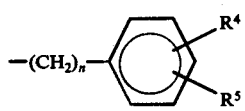

wherein n is an integer of 0 to 5, $R^4$ and $R^5$ are alike or different and each is H, Cl, Br, F, $CF_3$, $NO_2$, OH, (lower)alkyl or (lower)alkoxy.

Another preferred embodiment of the present invention is the compound having the formula

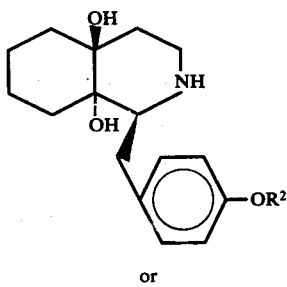

or

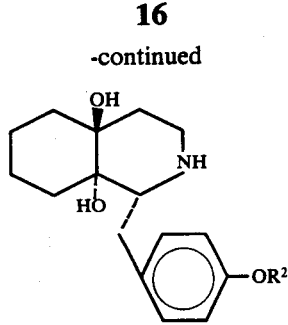

in which $R^2$ is (lower)alkyl.

A most preferred embodiment is the compound having the formula

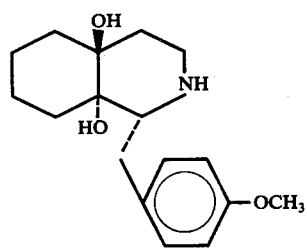

or

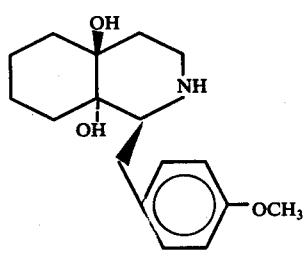

Another preferred embodiment is the compound having the formula

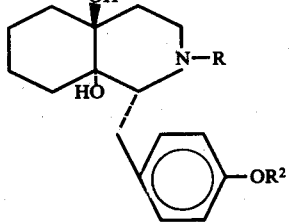

or

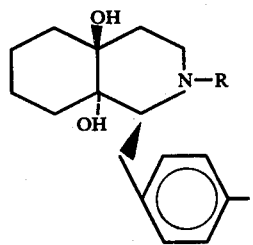

in which $R^2$ is (lower)alkyl, R is a radical of the formula

wherein X is H, CF₃, —OR³ or R³ in which R³ is (lower-)alkyl or a radical of the formula

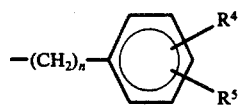

wherein n is an integer of 0 to 5 and R⁴ and R⁵ are alike or different and each is H, Cl, Br, F, CF₃, NO₂, OH, (lower)alkyl or (lower)alkoxy.

A more preferred embodiment is the compound having the formula

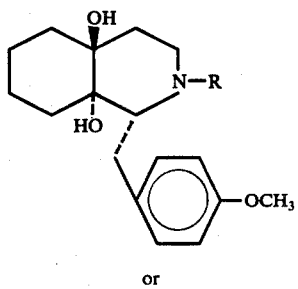

or

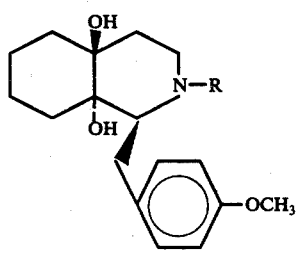

in which R is a radical having the formula

wherein X is H, CF₃ or OR³ in which R³ is (lower)-alkyl.

A most preferred embodiment is the compound having the formula

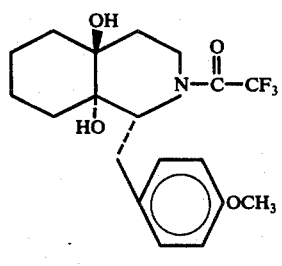

or

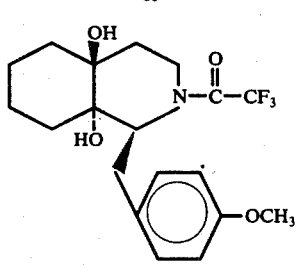

Another preferred embodiment is the compound having the formula

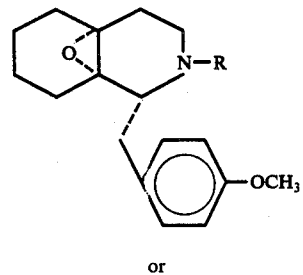

or

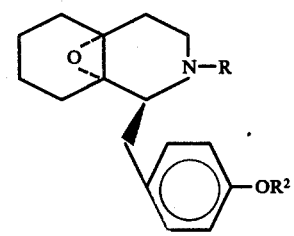

in which R² is (lower)alkyl and R is H or a radical having the formula

wherein X is H, CF₃, —OR³ or R³ in which R³ is (lower)-alkyl or a radical of the formula

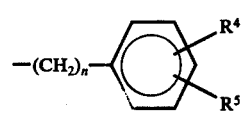

wherein n is 0 to 5 and R⁴ and R⁵ are alike or different and each is H, Cl, Br, F, CF₃, NO₂, OH, (lower)alkyl or (lower)alkoxy.

A more preferred embodiment is the compound having the formula

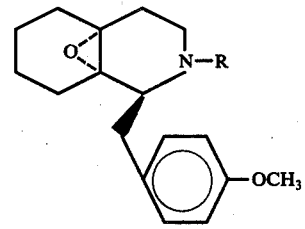

or

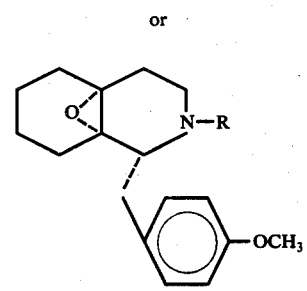

in which R is a radical of the formula

wherein X is H, CF₃ or OR³ in which R³ is (lower)alkyl.

A most preferred embodiment is the compound having the formula

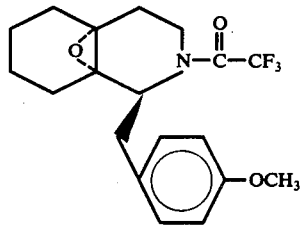

or

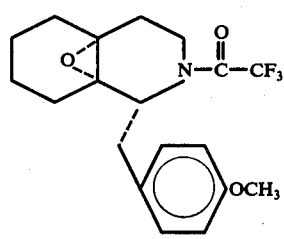

A more preferred embodiment is the compound having the formula

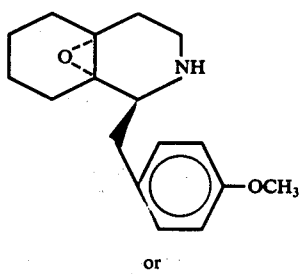

or

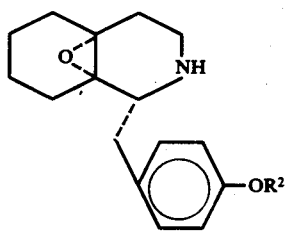

in which R² is (lower)alkyl.

A most preferred embodiment is the compound having the formula

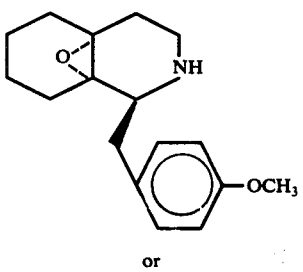

or

-continued

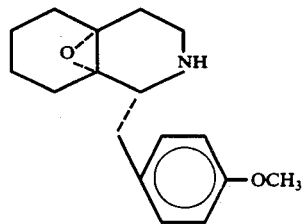

The term strong acid as used herein includes, but is not limited to, polyphosphoric acid, phosphoric acid, sulfuric acid, orthophosphoric acid, pyrophosphoric acid and mixtures thereof, and the like.

EXPERIMENTAL

All temperatures are expressed in degrees Centigrade unless otherwise stated. IR means infrared spectrum, NMR means nuclear magnetic resonance spectrum.

EXAMPLE 1

1-(p-methoxybenzyl)-2-trifluoroacetyl-1,2,3,4,5,6,7,8 octahydroisoquinoline (Ib)

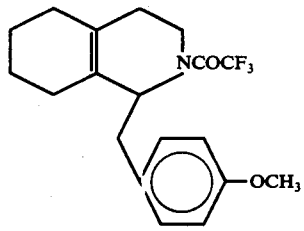

To a cooled (ice-bath) solution of 2-(p-methoxybenzyl)-1,2,3,4,5,6,7,8-octahydroisoquinoline (1.82 g., 7 mmoles) and triethylamine (0.73 g, 7.2 mmoles) in dichloromethane (15 ml) was added dropwise a solution of trifluoroacetic anhydride (0.51 g, 7.2 mmol) in dichloromethane (10 ml). The reaction mixture was washed successively with 1N hydrochloric acid, aqueous ammonia and water, and then it was dried and concentrated in vacuo to give 2.41 g (theoretical yield) of Ib as an oil; I.R. 1680 cm⁻¹, NMR (CDCl₃) δ6.5 − 7.0 (4H, m), 4.68 (1H, broad t, J = 6.5 Hz), 3.56 (3H, s, 2.5 − 3.9 (4H, m), 1.4 − 2.2 (10 H, m). Molecular weight calculated for $C_{19}H_{22}F_3NO_2$: 353, Found (mass spectrometry) 353.

EXAMPLE 2

Trans-9,10-Epoxy-1-(p-methoxybenzyl)-2-trifluoroacetylperhydroisoquinoline (IIb) and corresponding cis epoxide (IIIb)

IIb

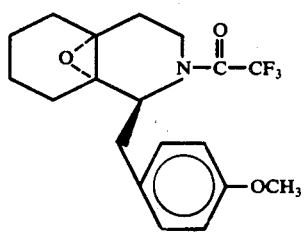

and

-continued

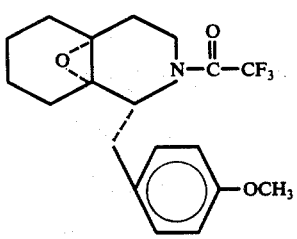
IIb

To a cooled (ice-salt) solution of Ib (3.8 g., 10.8 mmol) in dichloromethane (50 ml) was added portion-wise m-chloroperbenzoic acid (2.08 g., 12 mmoles). The mixture was stirred at room temperature for 18 hrs. following which the mixture was washed with 15% sodium bisulfate solution in water. The mixture was shaken vigorously following which it was washed with 5% sodium bicarbonate solution until the evolution of $CO_2$ ceased.

The dichloromethane phase was separated from the water phase, washed successively with water, and dried over anhydrous $Na_2SO_4$. Filtration, followed evaporation, gave 3.80 g. (94%) of a mixture of IIb and IIIb as an oil; IR 1790 cm$^{-1}$, Molecular Weight calc'd. for $C_{19}H_{22}F_3NO_3$: 369. Found (mass spectrometry) 369.

The mixture was separated by column chromatography (silica gel, eluent: benzene-ether) to obtain at first pure IIIb; m.p. 84°–86° from petroleum ether; NMR (CDCl$_3$) δ 6.5 – 7.1 (4H, m), 4.65 (1H, t, J = 7 Hz), 3.70 (3H, s), 2.5 – 3.5 (4H, m), 1.0 – 2.2 (10H, m).

Anal. calc'd. for $C_{19}H_{22}F_3NO_3$: C, 61.78; H, 6.00; N, 3.790 Found: C, 61.84; H, 6.05; N, 3.79.

The epimeric epoxide IIb was obtained next; m.p. 103°–105° C.; NMR (CDCl$_3$) δ6.8 – 7.2 (4H, m), 4.97 (1H, dd, $J_1$ = 5 Hz, $J_2$ = 8 Hz) 3.72 (3H, s), 2.6 – 3.6 (4H, m), 1.0–2.3 (10H, m).

Anal. calc'd. for $C_{19}H_{22}F_3NO_3$: C, 61.78; H, 6.00; N, 3.79. Found: C, 61.49; H, 5.95; N, 3.71. The ratio of IIIb to IIb was 7.3:1.

EXAMPLE 3

9,10-Epoxy-1-(p-methoxybenzyl)-perhydroisoquinolines (IIa and IIIa)

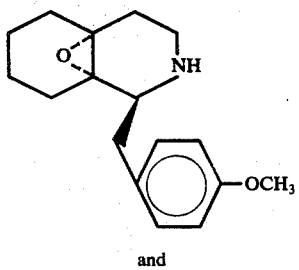
IIa and

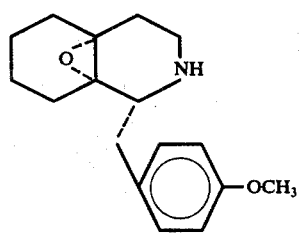
IIIa

To a solution of a mixture of IIb and IIIb (3.69 g., 10 mmoles) in absolute ethanol (20 ml) was added sodium borohydride (380 mg., 10 mmoles). The resulting suspension was refluxed for 25 mins., then it was evaporated to dryness. The residue was partitioned between ether and 1N hydrochloric acid. The aqueous phase was basified with ammonium hydroxide and extracted with methylene chloride. The methylene chloride was washed with water, dried and evaporated in vacuo to give 2.46 g. (90%) of essentially pure IIIa as an oil; NMR (CDCl$_8$) δ6.8–7.3 (4H, m) 3.8 (3H, s) 2.2–3.2 (5H, m), 1.1 – 2.1 (10H, m). Molecular weight calc'd. for $C_{17}H_{23}NO_2$: 273. Found: (mass spectrometry): 273. The ether extract contained mainly unhydrolyzed compound IIb.

EXAMPLE 4

9α, 10β-Dihydroxy-1α-(p-methoxybenzyl)perhydroisoquinoline (Va')

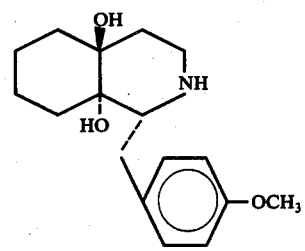
Va' and

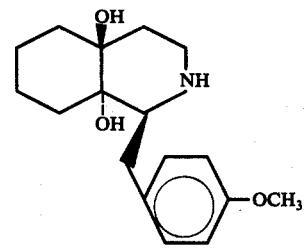
IVa'

To a solution of IIa (2.46 g., 9.01 mmoles) in tetrahydrofuran (25 ml) was added 20% perchloric acid (25 ml). The mixture was left at room temperature for 18 hours. It was then basified with ammonium hydroxide and extracted with benzene/ether (1:1). The organic layer was washed with water (2 × 10 ml), dried and evaporated in vacuo to give Va' [2.46 g. (94%)] as a solid containing a small amount of IV'a. Crystallization from acetone-ether gave an analytical sample; m.p. 154°–156° C. IR (CHCl$_3$) 3610, 3450 cm$^{-1}$, NMR (CDCl$_3$) δ6.8 – 7.3 (4H, m), 3.78 (3H, s), 2.2 – 3.3 (5H, m), 1.0–2.2 (10H, m).

Anal. calc'd. for $C_{17}H_{25}NO_3$: C, 70.07; H, 8.65; N, 4.81. Found: C, 70.28; H, 8.65; N, 4.78.

EXAMPLE 5

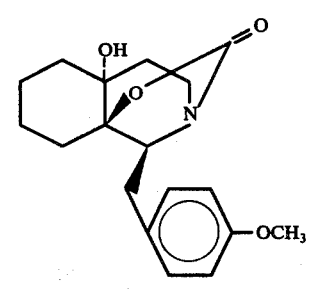
VIa' and

-continued

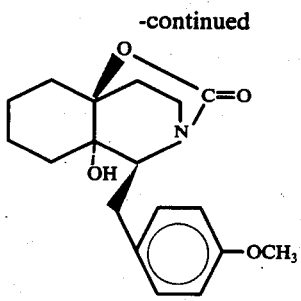

VIb'

Oxazolidone Intermediate (VIa' and VIb')

To a stirred, cooled (ice-bath) solution of a mixture of IVa' and Va' (0.582 g., 2 mmoles) in tetrahydrofuran (8 ml) was added triethylamine (0.61 ml. 4.4 mmoles), then it was treated dropwise by phosgene (1.90 ml., 2.2 mmoles of 12.5% in benzene) in tetrahydrofuran (3 ml). When the addition was completed, the ice-bath was removed and the solution was stirred at room temperature for 18 hours. At the end of this period, the mixture was partitioned between 0.2N HCl and benzene/ether (1:1, 10 ml) and the organic layer was washed with 1N NaHCO₃, dried and concentrated in vacuo to give 0.420 g. of a mixture of VIa' and VIb' as a white solid; m.p. 150°–154° C., I.R. 1680, 1775 cm⁻¹.

In a similar procedure, pure VIa' was obtained from Va'; m.p. 163°–165° C: An analytical sample was obtained by recrystallization from acetone-ether; m.p. 169°–170°, i.r. (CHCl₃), 3619, 3490, 1775 cm⁻¹, n.m.r. (CDCl₃) $\delta$6.7 – 7.4 (4H, m), 3.82 (3H, s), 2.0 – 4.0 (5H, m), 1.2–2.0 (10H, m).

Anal. Calc'd. for $C_{18}H_{23}NO_4$: C, 68.12; H, 7.30; N, 4.41. Found: C, 68.45; H, 7.40; N, 4.41.

EXAMPLE 6

14$\beta$-Hydroxy-3-methoxymorphinan (XX')

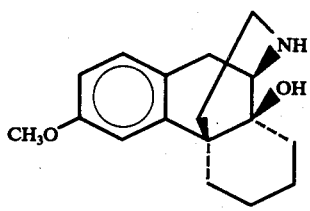

The mixture of oxazolidones VIa' and VIb+ (100 mg., 0.3 mmole) and polyphosphoric acid (2.0 g.) were mixed together and heated at 57° C. for seven days. The mixture was cooled, diluted with water (10 ml.) and extracted with chloroform (3 × 10). The aqueous layer was basified with concentrated ammonium hydroxide (3.5 ml) and extracted with benzene-ether (1:1). The benzene-ether extract was dried and evaporated in vacuo to give 12 mg (7%) of product XXa.

EXAMPLE 7

9$\alpha$,10$\beta$-Dihydroxy-1$\beta$-(p-methoxybenzyl)-2-trifluoroacetylperhydroisoquinoline (IVb) and isomeric (Vb)

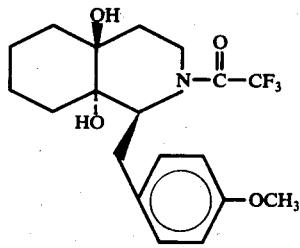

IVb and

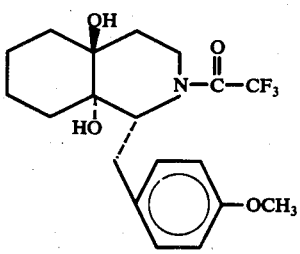

Vb

To a solution of a mixture of IIb and IIIb (2.80 g., 7.7 mmol) in THF [tetrahydrofuran, (20 ml)] was added 20% perchloric acid (10 ml) and the mixture allowed to stand at room temperature for 18 hours. It was then concentrated in vacuo to ca 15 ml and partitioned between ether and water. The ether layer was washed with water, dried and concentrated in vacuo to give 2.90 g. (95%) of a mixture of diols IVb and Vb respectively as an oil; IR 1680, 3480, 3600 cm⁻¹, NMR (CDCl₃) $\delta$6.6 – 7.3 (4H, m), 4.45 (1H, t, J = 8 Hz), 3.85 (3H, s), 3.5 – 3.9 (4H, m), 2.8 – 3.0 (2H, m), 1.0 – 2.5 (13H, m). Molecular weight calc'd. for $C_{19}H_{24}F_3NO_4$: 387. Found (mass spectrometry):387.

EXAMPLE 8

9$\alpha$, 10$\beta$-Dihydroxy-1$\beta$-(p-methoxybenzyl-perhydroisoquinoline (IVa) and isomeric (Va)

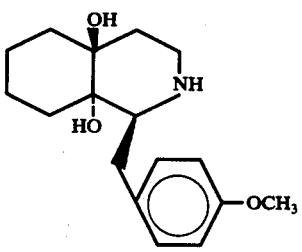

IVa and

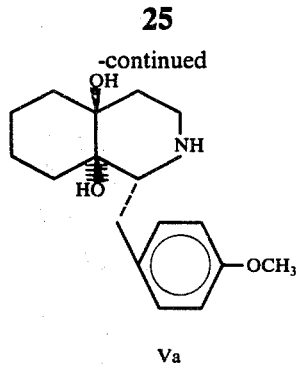

Va

To a solution of a mixture of IVb and Vb (5.36 g., 13.9 mmoles) in methanol (50 ml) was added 20% aqueous K₂CO₃ solution (100 ml), and the mixture was refluxed for 18 hours followed by concentration to a small volume. The concentrate was partitioned between water and ether, and the ether layer was extracted with 1N hydrochloric acid. The acidic extract was made basic with aqueous ammonia and the product was collected by filtration and washed with small amounts of acetone and ether to give 3.0 g (75%) of 6:4 mixture of IVa and Va; m.p. 126°-128°; IR 3400 cm⁻¹, NMR (CDCl₃) δ6.6 – 7.2 (4H, m) 3.7 (3H,s), 2.2–3.6 (5H, m), 1.0 – 2.2 (10 H, m).

Anal. calc'd. for $C_{17}H_{25}NO_3$: C, 70.07; H, 8.65; N, 4.81. Found: C, 70.28; H, 8.44; N, 4.84.

EXAMPLE 9

2-Formyl-1-(p-methoxybenzyl)-1,2,3,4,5,6,7,8-octahydroisoquinolne (Ic)

A solution of Ia (7.05 g., 27.4 mmoles) in ethyl formate (15.6 ml) was refluxed for 1 hour. The mixture was partitioned between water and methylene chloride. The organic layer was washed with diluted hydrochloric acid and with water, followed by drying and concentration in vacuo to give 5.6 g. (72%) of Ic as an oil; IR (CHCl₃) 1655 cm⁻¹, NMR (CDCl₃) δ7.97 and 7.47 (1H, singlets,

6.7 – 7.2 (3H, m), 4.1 – 4.9 (1H, m), 3.77 (3H, s), 2.3 – 3.7 (4H, m), 1.4 – 2.3 (10H, m). M.W. calc'd. for $C_{18}H_{23}NO_2$: 285. Found (mass spectrometry) 285.

EXAMPLE 10

9,10-Epoxy-2-formyl-1-(p-methoxybenzyl)-perhydroisoquinoline (IIc) and isomeric (IIIc)

To a cooled (ice-bath) stirred solution of Ic (8.0 g., 28.1 mmoles) in methylene chloride (150 ml) was added portionwise m-chloroperbenzoic acid (6.3 g., 31 mmoles). When the addition was completed, the reaction mixture was stirred for 1 hour at room temperature. Then it was washed successively with 15% sodium bisulfite, 5% sodium bicarbonate and water. Drying and evaporation of solvent gave an oil which crystallized from ether to give a mixture of IIc and IIIc as a white solid 6.7 g (80%); m.p. 94°-95° C.

Recrystallizaton from acetone/ether gave an analytical sample, M.P. 96°-97° C, I.R. (CHCl₃) 1655 cm⁻¹, NMR CDCl₃) δ7.90 and 7.35 (1H, singlets), 7.30–7.75 (4H, m), 4.7 and 3.9 – 4.4 (1H, t, J = 7 Hz and m), 3.78 (3H, s), 2.5 – 3.8 (4H, m), 1.1 – 2.2 (10H, m).

Anal. calc'd. for $C_{18}H_{23}NO_3$: C, 71.73; H, 7.69; N, 4.65.
Found: C, 71.51; H, 7.71; N, 4.58.

EXAMPLE 11

2-Formyl-9α,10β-dihydroxy-1β(p-methoxybenzyl)perhydroisoquinoline (IVc) and the corresponding 1α-isomeric (Vc)

To a solution of a mixture of IIC and IIIc (6.0 g, 20 mmoles) in THF (tetrahydrofuran) (60 ml) was added in room temperature 20% HClO₄ (60 ml). This solution was allowed to stand at room temperature for 5 hours, and then it was concentrated in vacuo. The residue was partitioned between methylene chloride and dilute aqueous ammonia. The organic layer was washed with water, dried and evaporated in vacuo, followed by treatment with ether to give 4.9 g (77%) of a mixture of IVc and Vc as a white solid; m.p. 225°-226° C.

Recrystallization from methanol gave an analytical sample: M.P. 227°-228° C., IR (nujol) 3200-3600 cm⁻¹, 1635 cm⁻¹, (CdCl₃) 7.8 and 7.12 (1H, singlets), 6.5-7.05 (4H, m), 3.5-4.32 (3H, m), 3.67 (3H, s), 2.66-3.48 (4H, m), 0.9 – 2.3 (10H, m).

Anal. calc'd. for $C_{18}H_{25}NO_4$: C, 67.69; H, 7.87; N, 4.83. Found: C, 67.94; H, 7.87; N, 4.30.

EXAMPLE 12

2-Carbomethoxy-1-(p-methoxybenzyl)-1,2,3,4,5,6,7,8-octahydroisoquinoline (Id)

To a cooled (ice-bath) stirred solution of Ia (5.3 g., 20 mmoles) in methylene chloride (25 ml) containing 5 ml of tetrahydrofuran and triethylamine (6 ml) was added dropwise a solution of methyl chloroformate (3.78 g., 40 mmoles) in methylene chloride (25 ml). The mixture was stirred at room temperature for 30 minutes and then it was washed with 1N hydrochloric acid and water, followed by drying and evaporation in vacuo. The residue was taken up in benzene and filtered over a Celite-charcoal bed and evaporated in vacuo to give 6.5 g (quantitative yield) of Id as an oil. Distillation at 175° C/1.0 mmHg gave an analytical sample I.R. (CHCl₃) 1685 cm⁻¹, NMR (CDCl₃) δ6.5 – 7.0 (4H, m), 4.0 – 4.4 (1H, m), 3.62 (3H, s), 3.20 and 3.45 (3H, broad singlets), 2.5 – 3.9 (4H, m), 1.4 – 2.2 (10H, m).

Anal. calc'd. for $C_{19}H_{25}NO_3$: C, 72.35; H, 7.99 N, 4.44. Found: C, 72.21; H, 8.22; N, 4.53.

EXAMPLE 13

2-Carbomethoxy-9,10-epoxy-1-(p-methoxybenzyl)perhydroisoquinoline (IId) and isomeric (IIId)

To a cooled (ice-bath) stirred solution of Id (6.0 g., 10 mmoles) in methylene chloride (100 ml) was added portionwise m-chloroperbenzoic acid (4.06 g., 20 mmoles). When the addition was completed, the reaction mixture was stirred for 1 hour at room temperature, then it was washed successively with 10% sodium bisulfite, 5% sodium bicarbonate and water. Drying and evaporation of solvent gave 6.3 g (quantitative yield) of a mixture of IId and IIId, as an oil. Distillation at 170°-175° C/0.12 mmHg gave an analytical sample IR (CHCl₃) 1690 cm⁻¹, NMR (CDCl₃) δ6.5-7.1 (4H, m), 4.0-4.6 (1H, m), 3.68 (3H, s), 3.25 and 3.53 (3H broad singlets), 2.5 – 3.8 (4H, m), 1.1 – 2.0 (10H, m).

Anal. calc'd. for $C_{19}H_{25}NO_4$: C, 68.86; H, 7.60 N, 4.23.

Found: C, 68.94; H, 7.45; N, 4.21.

EXAMPLE 14

2-Carbomethoxy-9α,10β-dihyddroxy-1β-(p-methoxybenzyl)-perhydroisoquinoline (IVd) and the corresponding 1α-isomeric (Vd)

To a solution of a mixture of IId and IIId (5.0 g., 15.1 mmoles) in tetrahydrofuran (50 ml) was added at room temperature 20% HClO$_4$ (50 ml). This solution was allowed to stand at room temperature for 5 hours and then it was concentrated in vacuo. The residue was partitioned between methylene chloride and dilute aqueous ammonia. The organic layer was washed with water, dried and evaporated in vacuo. The residue was treated with ether to give 4.6 g (87.7%) of a mixture of IVd and Vd as a white solid, M.P. 165°–166° C. Recrystallization from methanol gave an analytical sample m.p. 166°–167° C., I. R. (CHCl$_3$), 3600 cm$^{-1}$, 3300–3550 cm$^{-1}$, 1680 cm$^{-1}$, NMR (CDCl$_3$) δ6.42–7.05 (4H, m), 3.57–4.1 (1H, m), 3.65 (3H, s), 3.3 and 3.05 (3H singlets), 2.3–3.55 (6H, m), 0.9 – 2.3 (10H, m).

Anal. Calc'd. for C$_{19}$H$_{27}$NO$_5$: C, 65.31; H, 7.79; N, 4.01. Found: C, 65.52; H, 7.95; N, 4.11.

EXAMPLE 15

14-hydroxy-3-methoxymorphinan (XX!) and 3-methoxy-Δ$^{8,14}$-morphinan (XXI') from a mixture of IVc and Vc A mixture of N-formul diols IVc and Vc (1.70 g., 5.3 mmole) of phosphoric acid (34 g) was heated at 70° C for 19 hours, after which time it was poured into ice-water and extracted with chloroform (3 × 40 ml). The water layer was filtered with charcoal and the filtrate was made basic with ammonium hydroxide. Extraction with benzene-ether (1:1, 3 × 50 ml) followed by drying and concentration in vacuo afforded 390 mg of an oil. This was chromatographed over silica gel column (6 g., eluent methanol- NH$_3$) to give first 70 mg of crude XXI', followed by 120 mg of crude XX'. Further purification by treatment with charcoal and formation of oxalate salt gave 105 mg (5.3%) of XX' oxalate; m.p. 225°–227°. Recrystallization methanol afforded an analytical sample; M.P. 227°–228°.

Anal. calc'd. for C$_{17}$H$_{23}$NO$_2$·½C$_2$H$_2$O$_4$: C, 67.90; H, 7.59; N, 4.39. Found: C, 68.06; H, 7.73; N, 4.59. Purification of XXI gave 41 mg 82.4% of XXI' oxalate; M.P. 280°–282°).

Similar yields of XX' and XXI' were obtained by treatment of mixtures of IIb and IIIb, IVb and Vb, and IVd and Vd respectively with phosphoric acid.

EXAMPLE 16

Preparation of XX' and XXI' from IVc and Vc

Substitution in the procedure of example 15 for the IVd and Vd used therein of an equimolar quantity of IVc and Vc produces the title compound.

EXAMPLE 17

Preparation of Xx' and XXI' from IVb and Vb

Substitution in the procedure of example 15 for the IVb and Vb used therein of an equimolar quantity of IVb and Vb produces the title compound.

We claim:
1. A compound having the formula

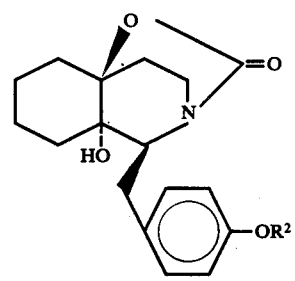

in which R$^2$ is loweralkyl.

2. The compound of claim 1 in which R$^2$ is methyl.

* * * * *